US009179852B2

(12) United States Patent
Audet et al.

(10) Patent No.: US 9,179,852 B2
(45) Date of Patent: Nov. 10, 2015

(54) HEART MONITORING SYSTEMS, APPARATUS AND METHODS ADAPTED TO DETECT MYOCARDIAL ISCHEMIA

(75) Inventors: Sarah A. Audet, Shoreview, MN (US); James K. Carney, Brooklyn Park, MN (US); William J. Combs, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 2455 days.

(21) Appl. No.: 11/684,794

(22) Filed: Mar. 12, 2007

(65) Prior Publication Data

US 2008/0228094 A1    Sep. 18, 2008

(51) Int. Cl.
*A61B 5/04* (2006.01)
*A61B 5/0452* (2006.01)
*A61B 5/0402* (2006.01)
*A61B 5/00* (2006.01)

(52) U.S. Cl.
CPC ............. *A61B 5/0452* (2013.01); *A61B 5/0006* (2013.01); *A61B 5/0031* (2013.01); *A61B 5/0402* (2013.01); *A61B 5/7475* (2013.01); *A61B 5/721* (2013.01)

(58) Field of Classification Search
CPC .. A61B 5/0006; A61B 5/0402; A61B 5/0031; A61B 5/0452; A61B 5/721
USPC .......................... 600/508, 513, 528; 607/4, 9
See application file for complete search history.

(56) References Cited

U.S. PATENT DOCUMENTS

| | | | |
|---|---|---|---|
| 6,501,983 B1 | 12/2002 | Natarajan et al. | |
| 6,942,622 B1 * | 9/2005 | Turcott | 600/508 |
| 7,130,681 B2 | 10/2006 | Gebhardt et al. | |
| 7,181,268 B2 | 2/2007 | Sheldon et al. | |

(Continued)

FOREIGN PATENT DOCUMENTS

| | | |
|---|---|---|
| WO | 03/020367 A1 | 3/2003 |
| WO | WO2004103150 A | 12/2004 |

OTHER PUBLICATIONS

Gersh, Bernard J., "Pharmacological Facilitation of Primary Percutaneous Coronary Intervention for Acute Myocardial Infarction," JAMA, Feb. 23, 2005, vol. 293, No. 8, pp. 979-986.
Goldberg, Robert J., "Duration of, and Temporal Trends (1994-1997) in, Prehospital Delay in Patients With Acute Myocardial Infarction: The Second National Registry of Myocardial Infarction," Archives of Internal Medicine, Oct. 1999; vol. 159, pp. 2141-2147.
(EP10015639.7) European Extended Search Report dated Apr. 4, 2011, 6 pages.

(Continued)

*Primary Examiner* — Christopher D Koharski
*Assistant Examiner* — Pamela M Bays
(74) *Attorney, Agent, or Firm* — Michael J. Ostrom

(57) ABSTRACT

Embodiments include heart monitoring systems, apparatus, and methods adapted to detect myocardial ischemia. An apparatus includes at least one first-tier sensor/analyzer adapted to sense a first input related to cardiac function, and to produce a first-tier trigger signal when the first input indicates myocardial ischemia. In an embodiment, a first-tier sensor/analyzer includes an ECG sensor/analyzer. In another embodiment, a first-tier sensor/analyzer includes a patient activator. An apparatus further includes at least one second-tier sensor/analyzer adapted to sense a second input related to cardiac function, and to produce a second-tier trigger signal when the second input indicates myocardial ischemia. In an embodiment, a second-tier sensor-analyzer includes a heart sound sensor/analyzer. A triggering element is adapted to produce a response-invoking signal in response to the first-tier trigger signal and the second-tier trigger signal. The response-invoking signal may invoke a patient alert, a message to an external system, and/or a cardiac stimulus.

23 Claims, 7 Drawing Sheets

(56) References Cited

U.S. PATENT DOCUMENTS

| | | |
|---|---|---|
| 2003/0158492 A1 | 8/2003 | Sheldon et al. |
| 2004/0122478 A1 | 6/2004 | Stadler et al. |
| 2006/0106322 A1 | 5/2006 | Arand et al. |
| 2006/0282000 A1* | 12/2006 | Zhang et al. .................. 600/528 |
| 2007/0250127 A1 | 10/2007 | Stylos et al. |
| 2007/0255151 A1 | 11/2007 | Struble et al. |
| 2007/0299356 A1 | 12/2007 | Wariar et al. |

OTHER PUBLICATIONS

Office Action for U.S. Appl. No. 12/181,247, Mailed Jul. 26, 2011, 16 pages.
Response to Office Action for U.S. Appl. No. 12/181,247, Submitted on Nov. 28, 2011, 10 pages.
Final Office Action for U.S. Appl. No. 12/181,247, Mailed Jun. 21, 2013, 12 pages.

\* cited by examiner

HEART MONITORING SYSTEMS, APPARATUS AND METHODS ADAPTED TO DETECT MYOCARDIAL ISCHEMIA

TECHNICAL FIELD

Embodiments of the inventive subject matter relate to heart monitoring systems, apparatus, and methods, and more particularly to heart monitoring systems, apparatus, and methods adapted to detect myocardial ischemia.

BACKGROUND

Coronary artery disease is a disease of the coronary arteries, which causes decreased blood flow to the heart muscle. Individuals with coronary artery disease (or other conditions) may experience myocardial ischemia, which is an imbalance between myocardial oxygen demand and myocardial oxygen supply. In some cases, myocardial ischemia may result in irreversible cardiac cell death (e.g., cell necrosis), a result commonly referred to as a myocardial infarction. Acute myocardial infarction (AMI) is the acute phase of a myocardial infarction (MI), during which cell necrosis occurs. Along with coronary artery disease, other conditions also may result in myocardial ischemia and/or AMI. For example, myocardial ischemia may result from cardiovascular disease, ischemic heart disease, pulmonary heart disease, hereditary heart disease, hypertensive heart disease, inflammatory heart disease, valvular heart disease, atherosclerosis, tachycardia, hypertension, hypotension, thromboembolism, compression of a blood vessel or artery (e.g., by a tumor), foreign matter within the cardiovascular system, sickle cell disease, and/or other causes. Minimizing the time to diagnose an ST segment elevated AMI (STEMI) and to provide treatment is critical to preventing damage to the cardiac tissue and death. Diagnoses and treatment within the first hour after a STEMI AMI event have been shown to abort MI (See *JAMA, GERSH*, Bernard J., "*Pharmacological Facilitation of Primary Percutaneous Coronary Intervention for Acute Myocardial Infarction,*" *JAMA*, Feb. 23, 2005, Vol. 293, No. 8, pages 979-986, and GOLDBERG, Robert J., "*Duration of, and Temporal Trends (1994-1997) in, Prehospital Delay in Patients With Acute Myocardial Infarction: The Second National Registry of Myocardial Infarction,*" *Archives of Internal Medicine*, October 1999; Vol. 159, pages 2141-2147.).

Acute coronary syndrome, commonly referred to as a "heart attack," refers to the series of events associated with coronary vessel closure or occlusion. The series of events may proceed from stable angina (e.g., chest/arm pain or dyspnea with exertion) to unstable angina (e.g., chest/arm pain at rest or increasing frequency of angina). Acute coronary syndrome may then proceed to an AMI and death, in some cases. Myocardial ischemia is present at the onset of acute coronary syndrome, and may indicate the potential for an impending AMI.

Myocardial ischemia may be transient, sub-lethal or persistent. Transient myocardial ischemia may have a relatively short duration (e.g., minutes), with prompt reperfusion of the coronary blood vessels. Accordingly, cell necrosis does not typically occur with transient myocardial ischemia. Sub-lethal myocardial ischemia may have a significantly longer duration (e.g., weeks or months), although it also is characterized by subsequent reperfusion and no cell necrosis. Persistent myocardial ischemia, during which no reperfusion occurs of the coronary blood vessels, may result in cell necrosis and death.

An individual may experience physical symptoms warning them of the onset or presence of transient, sub-lethal or persistent myocardial ischemia. These warning symptoms may include, for example, chest and/or arm pain (e.g., stable angina or unstable angina), shortness of breath, nausea, vomiting, palpitations, sweating, weakness, fatigue, anxiety, and/or one or more other physical symptoms. Through education, many people realize that they should promptly seek medical attention at the onset of such physical symptoms. However, a significant number of individuals experience non-specific symptoms or "silent" myocardial ischemia, during which they do not perceive any physical symptoms of myocardial ischemia. Accordingly, an acute coronary syndrome for such an individual may proceed to an AMI before this individual becomes inclined to seek medical attention.

When medical personnel (e.g., emergency room personnel) are presented with a patient who exhibits symptoms of myocardial ischemia, the conventional standard of care includes applying current AMI detection apparatus and methods. Typically, this includes monitoring the bioelectrical impulses from the patient's heart using an electrocardiogram (ECG), and looking for certain characteristics of the ECG waveform. A typical ECG may have as many as twelve leads, and this system may have only about 50% sensitivity to the detection of an on-going AMI at the time the patient first arrives at the emergency room. Accordingly, the patient's heart rate and certain cardiac biomarkers, present in the blood, also may be monitored. However, cardiac biomarkers associated with severe ischemia typically are not produced in significant quantities until cell necrosis has occurred, and it may take several hours for the biomarker concentrations to reach measurable levels.

When an impending or current AMI is diagnosed, therapies may include thrombolytic therapy and/or administering aspirin, beta-blockers, nitrates, and/or statins, among other things. These therapies, when administered promptly and properly, may minimize or stop cell necrosis. Accordingly, an individual experiencing myocardial ischemia, particularly persistent myocardial ischemia, is well advised promptly to seek medical attention, in order to reduce the occurrence or severity of cell necrosis and, in some cases, to avoid death. However, a patient may delay early action due to denial, psychological factors, and/or physical factors. In addition medical personnel may delay early treatment because of the time required for running diagnostic tests.

For at least the foregoing reasons, a need exists for methods and apparatus to detect the onset or presence of myocardial ischemia, and to provide more accurate and timely cardiac monitoring in the presence of myocardial ischemia.

BRIEF SUMMARY

An embodiment of the inventive subject matter includes a heart monitoring apparatus adapted to detect myocardial ischemia. The apparatus includes at least one first-tier sensor/analyzer adapted to sense a first input related to cardiac function, and to produce a first-tier trigger signal when the first input indicates myocardial ischemia. In addition, the apparatus includes at least one second-tier sensor/analyzer adapted to sense a second input related to cardiac function, and to produce a second-tier trigger signal when the second input indicates myocardial ischemia. In addition, the apparatus includes a triggering element adapted to produce a response-invoking signal in response to the first-tier trigger signal and the second-tier trigger signal.

Another embodiment of the inventive subject matter includes a heart monitoring apparatus having an electrocardiogram (ECG) sensor/analyzer adapted to sense bioelectrical activity, to produce a current ECG waveform, and to produce an ECG trigger signal when at least a portion of the current ECG waveform indicates myocardial ischemia. In addition, the apparatus includes a heart sound sensor/analyzer adapted to sense heart sounds, to produce a current heart sound waveform, and to produce a heart sound trigger signal when at least a portion of the current heart sound waveform indicates the myocardial ischemia. In addition, the apparatus includes a triggering element adapted to produce a response-invoking signal in response to the ECG trigger signal and the heart sound trigger signal.

Yet another embodiment of the inventive subject matter includes a method for heart monitoring adapted to detect myocardial ischemia. The method includes the steps of sensing at least one first input related to cardiac function, sensing at least one second input related to cardiac function when at least one first input indicates myocardial ischemia, and producing a patient alert when the at least one second input also indicates the myocardial ischemia.

BRIEF DESCRIPTION OF THE DRAWINGS

The inventive subject matter will be described in conjunction with the following drawing figures, in which.

DETAILED DESCRIPTION

The following detailed description of the inventive subject matter is merely exemplary in nature and is not intended to limit the inventive subject matter or the application and uses of the inventive subject matter. Furthermore, there is no intention to be bound by any theory presented in the preceding background or the following detailed description.

Embodiments of the inventive subject matter include systems, apparatus, and methods adapted to detect the onset or presence of myocardial ischemia. In particular, embodiments include systems, apparatus, and methods adapted to sense and analyze one or more of various physical, bioelectrical, biological, and/or chemical events that may indicate the onset or presence of myocardial ischemia. In a particular embodiment, which will be described in detail later, a myocardial ischemia detection apparatus may include an ECG sensing apparatus and a heart sound sensing apparatus. In various embodiments, a myocardial ischemia detection apparatus may include one or more additional sensing/analysis apparatus, including but not limited to one or more vibration sensors, pressure sensors, change in pressure with time (dp/dt) sensors, magnetic sensors, biomarker level sensors (e.g., cardiac troponin I and T, creatine phosphokinase, creatine phosphokinase myoglobin band, myoglobin, fatty acid binding protein, ischemia modified albumin, and/or lactic acid sensors), oxygen level sensors, carbon dioxide level sensors, glucose sensors, pH sensors, body temperature sensors, heart rate sensors, heart rate variability sensors, heart wall motion sensors, impedance sensors, optical sensors, respiration sensors, and/or patient activators, to name a few. A myocardial ischemia detection apparatus may be a stand-alone apparatus, or it may be incorporated into a host system, such as an implantable pulse generator (IPG, also known as a "pacemaker"), an implantable cardiac resynchronization therapy device (CRT), an implantable cardioverter defibrillator (ICD), an implantable cardiac diagnostic and monitoring device, a unit that combines two or more of the aforementioned devices, or another device. In addition or alternatively, a myocardial ischemia detection apparatus and/or a host system may communicate with one or more remote devices, as will be described in more detail later. In order to describe embodiments of the inventive subject matter clearly, a description of a human heart and its functioning is included below.

Figure 1:
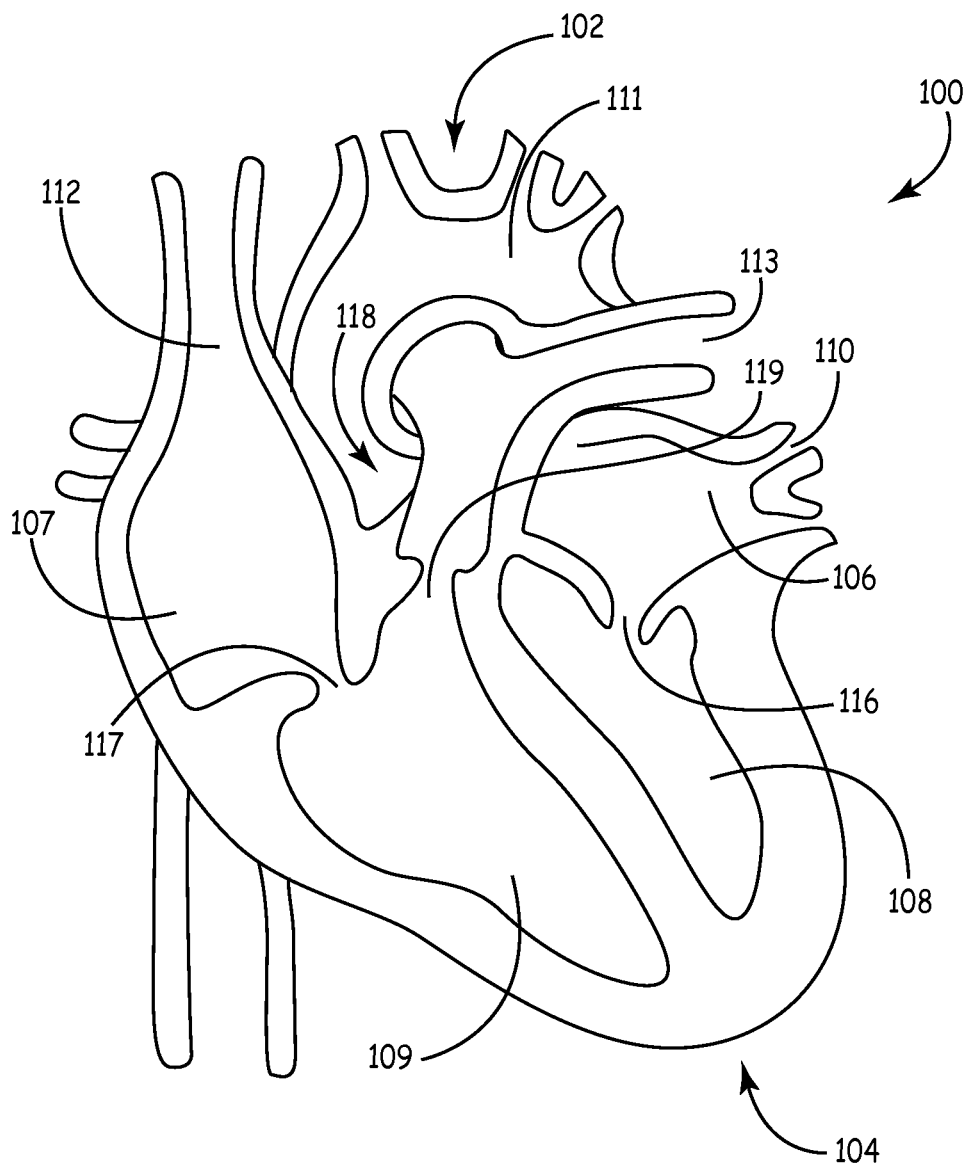
FIG. 1 illustrates the interior anatomy of a human heart.

FIG. 1 illustrates the interior anatomy of a human heart 100. The top of the heart 100 may be referred to as the base 102, and the bottom of the heart may be referred to as the apex 104. The heart 100 includes four chambers: a left atrium 106, a right atrium 107, a left ventricle 108, and a right ventricle 109. During a cardiac cycle, the heart chambers 106-109 contract and relax in response to electrical currents periodically conveyed by a biological conduction system (not illustrated).

During a portion of the cardiac cycle referred to as diastole, the left atrium 106 relaxes and fills with blood from the lungs via the upper pulmonary vein 110 (i.e., pulmonary veins from the left and right lungs). The right atrium 107 also relaxes during diastole, and fills with blood from the body via the superior vena cava 112 and the inferior vena cava (not shown in FIG. 1). The blood within the left atrium 106 enters the left ventricle 108 through the mitral valve 116. The left ventricle 108 subsequently pumps the blood through the aortic valve 118 (hidden in FIG. 1) and into the body via the aorta 111 during a phase of the cardiac cycle referred to as systole.

During a portion of the cardiac cycle referred to as diastole, the blood within the right atrium 107 enters the right ventricle 109 through the tricuspid valve 117. The right ventricle 109 subsequently pumps the blood through the pulmonary valve 119 and into the lungs via the pulmonary artery 113 during systole.

The set of four heart valves function to regulate blood flow through the chambers 106-109 of the heart 100, by opening and closing at various times. These valves include the atrio-ventricular (AV) valves 116, 117 and the semilunar (SL) valves 118, 119. The AV valves include the mitral valve 116 and the tricuspid valve 117. The AV valves 116, 117 open during diastole to allow the ventricles to fill with blood. The SL valves 118, 119, which are set between the arteries 106, 107 and the ventricles 108, 109, include the aortic valve 118 and the pulmonary valve 119. The SL valves 118, 119 open during systole to allow blood to be ejected from the heart 100.

During a cardiac cycle (i.e., a heartbeat), a sequence of events occurs within the heart 100, as described above. As mentioned previously, each cardiac cycle includes a diastole portion and a systole portion. More specifically, each cardiac cycle includes three major stages: atrial systole; ventricular systole; and complete cardiac diastole. These three stages may be monitored by an ECG, which senses the pattern of electrical impulses generated at the heart during the stages of the cardiac cycle. A series of "heart sounds" (also referred to as "heart tones"), which occur synchronously with corresponding portions of an ECG, also may be sensed and represented by a sound waveform.

Figure 2:
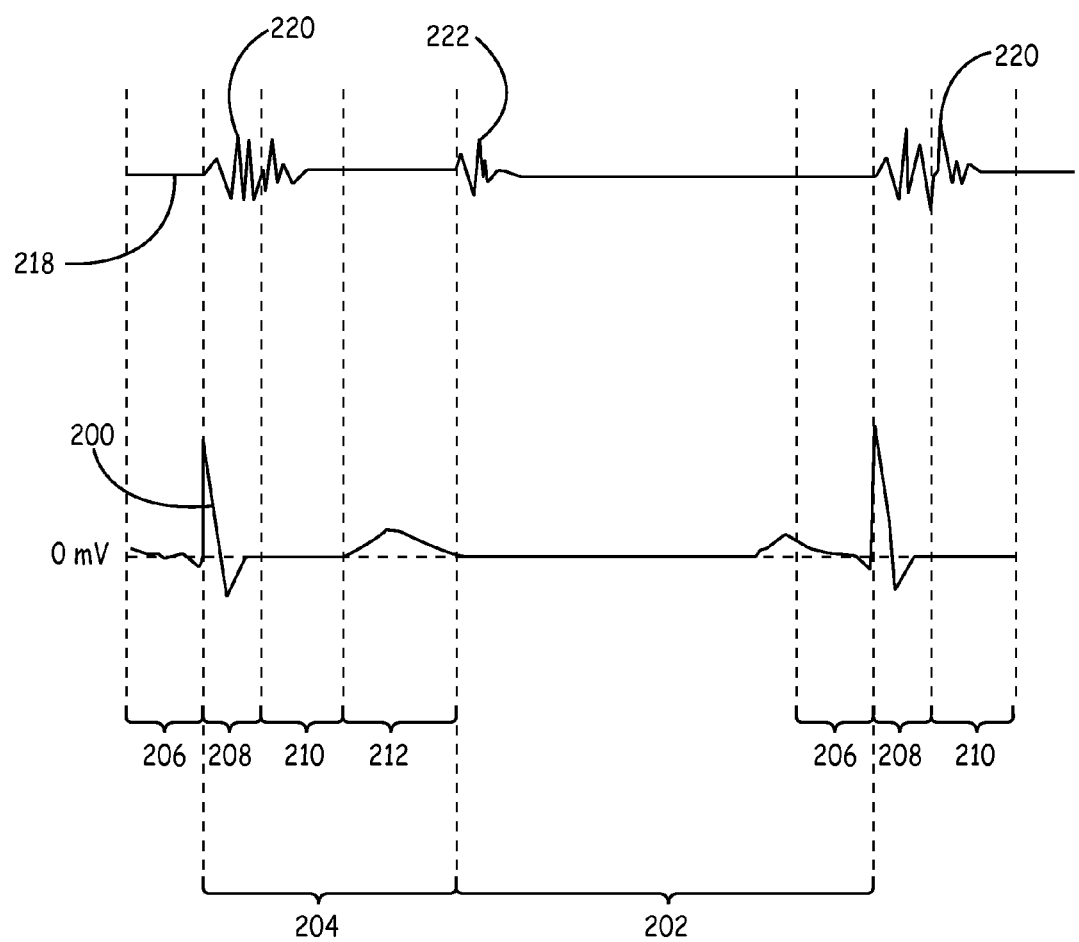
FIG. 2 illustrates an ECG waveform and a corresponding sound waveform for two normal cardiac cycles.

FIG. 2 illustrates an ECG waveform 200 and a corresponding sound waveform 218 for two normal cardiac cycles. A cardiac cycle includes TR segment 202 and a QT segment 204. The TR segment 202 includes a P wave 206. The P wave 206 indicates the movement of electrical activity through the upper heart chambers. Atrial systole occurs at the onset of the P wave 206, and indicates the contraction of the myocardium (i.e., heart muscle tissue) of the left and right atria. Atrial systole includes an electrical systole (i.e., the electrical activity that stimulates contraction of the myocardium of the heart chambers) followed by a mechanical systole (i.e., the mechanical contraction of the heart chambers).

Complete cardiac diastole occurs during the TR segment 202, and indicates the relaxation of the heart muscle after contraction in preparation for refilling with circulating blood. Complete cardiac diastole includes a ventricular diastole period when the ventricles are relaxing, and an atrial diastole period when the atria are relaxing. During the ventricular diastole period, the blood pressure in the left and right ventricles drops from the peak that it reached in systole. When the pressure in the left ventricle drops to a pressure below the pressure in the left atrium, the mitral valve opens, and the left ventricle fills with the blood that was accumulating in the left atrium. Likewise, when the pressure in the right ventricle drops below the pressure in the right atrium, the tricuspid valve opens, and the right ventricle fills with the blood that was accumulating in the right atrium.

The QT segment 204 of a cardiac cycle includes a QRS complex 208, ST segment 210, and T wave 212. The ST segment 210 normally appears as a straight, level line between the QRS complex 208 and the T wave 212. The T wave 210 corresponds to the period when the lower heart chambers are relaxing electrically and preparing for their next muscle contraction.

Ventricular systole occurs during QT segment 204, and indicates the contraction of the myocardium of the left and right ventricles. Similar to atrial systole, ventricular systole also includes an electrical systole followed by a mechanical systole. In an ECG 200, electrical systole of the ventricles begins at the beginning of the QRS complex 208 (i.e., a measurement of the movement of electrical impulses through the lower heart chambers).

During a cardiac cycle, many distinct heart sounds may be audible. Two of these heart sounds, represented along sound wave 218, are referred to as the first heart sound 220 (S1) and the second heart sound 222 (S2). The third heart sound (S3) and the fourth heart sound (S4) will be discussed in conjunction with FIG. 3, later. As used herein, an "auscultation area" refers to an area of the heart or the body where a sensor may be placed to sense the heart sounds.

The first heart sound 220 is associated with the closing of the mitral and tricuspid valves (i.e., the AV valves) at the beginning of ventricular systole. The first heart sound 220 is the first part of the "lub-dup" sound of a heartbeat. The second heart sound 222 is associated with the closing of the aortic and pulmonic valves (i.e., the SL valves) at the end of ventricular systole. The second heart sound 222 is the second part of the "lub-dup" sound of a heartbeat. At the end of ventricular systole, as the left ventricle relaxes, its pressure falls below the pressure in the aorta, and the aortic valve closes. Similarly, as the pressure in the right ventricle falls below the pressure in the pulmonary artery, the pulmonic valve closes. In a normal sequence, the aortic valve closes a few milliseconds before the pulmonic valve.

Figure 3:
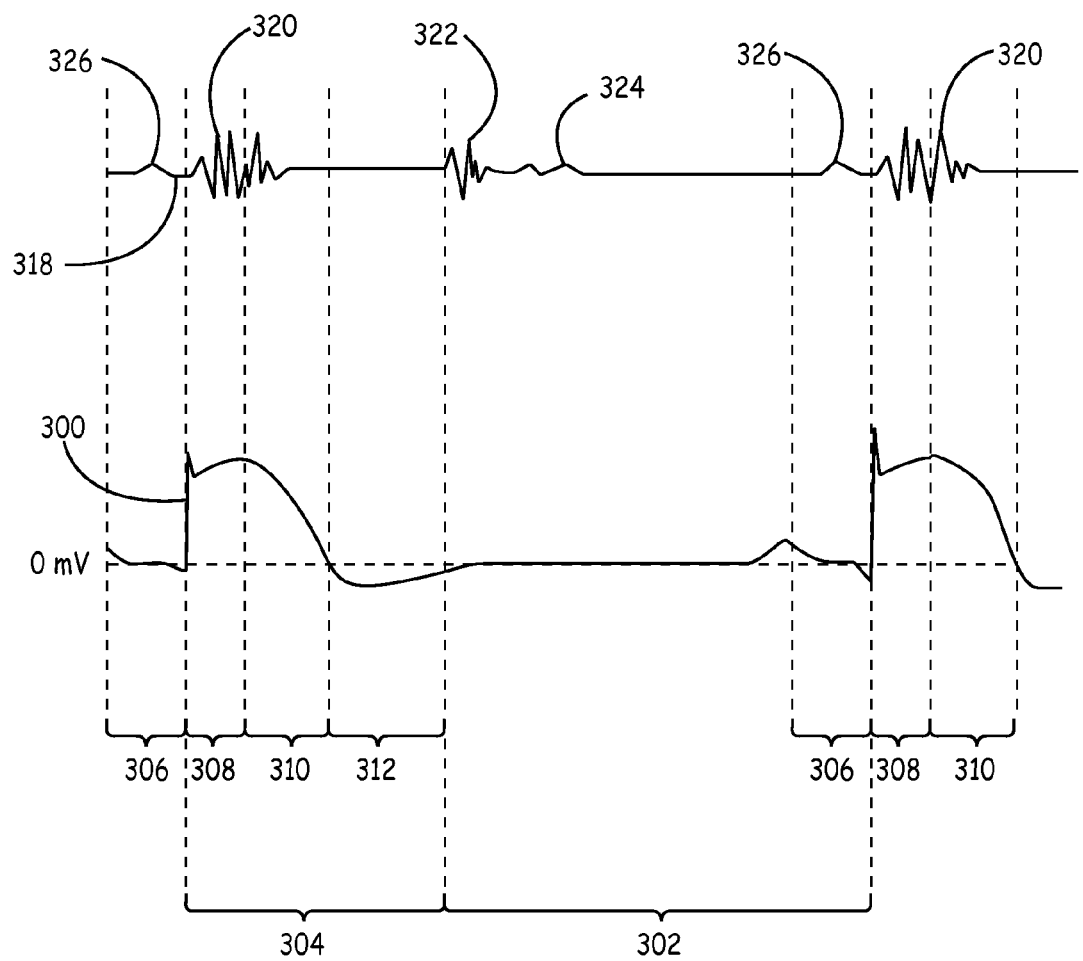
FIG. 3 illustrates an ECG waveform and a corresponding sound waveform for two cardiac cycles that are characteristic of myocardial ischemia.

FIG. 3 illustrates an ECG waveform 300 and a corresponding sound waveform 318 for two cardiac cycles that are characteristic of myocardial ischemia. As mentioned previously, during a cardiac cycle, multiple distinct heart sounds may be audible. A first heart sound 320 and a second heart sound 322 are illustrated in FIG. 3, along with a third heart sound 324 and a fourth heart sound 326. The third heart sound 324 and fourth heart sound 326 may be considered as "extra" heart sounds, because they are not always produced.

The third heart sound 324, which may also be referred to as "S3 gallop," "ventricular gallop," or "postdiastolic gallop," occurs during the filling phase of diastole. The third heart sound 324 is a low pitch sound, and may best be sensed at an auscultation site near the apex (104, FIG. 1) of the heart, although it may be sensed elsewhere, as well. The third heart sound 324 may be heard just after (e.g., about 140-160 milliseconds after) the second heart sound 322. The third heart sound 324 occurs in early diastole, during the time of rapid ventricular filling.

The third heart sound 324 is considered normal in children and young adults. However, when heard in individuals over the age of 40, it may reflect a pathological heart disorder characterized by ventricular dilatation, decreased systolic function, and/or elevated ventricular diastolic filling pressure. A pathological third heart sound 324 may indicate mitral stenosis, coronary artery disease with associated ischemia, cardiomyopathies, incompetent valves, left to right shunts, ventricular septal defects (VSD), or Patent Ductus Arteriosus (PDA), and/or congestive heart failure. The third heart sound 324 also may be seen in the absence of a pathological heart disorder, such as when an individual has hyperthyroidism or pregnancy.

The fourth heart sound 326, which may also be referred to as "S4 gallop," "atrial gallop," or "presystolic gallop," is a very soft, low frequency, filling sound heard just before the first heart sound 320. The fourth heart sound 326 is a diastolic sound, occurring during the late diastolic filling phase at the time when the atria contract. The fourth heart sound 326 may have its origin in either the left or right sides of the heart. A fourth heart sound 326 of left ventricular origin may best be sensed at an auscultation site near the apex (104, FIG. 1). A fourth heart sound 326 of right ventricular origin may best be sensed at the left lateral sternal border, although it may be sensed elsewhere, as well.

The fourth heart sound 326 may be considered normal in children, but may be considered abnormal (i.e., pathological) after the age of 20. A pathological fourth heart sound 326 may be present when the ventricles have a decreased compliance, or are receiving an increased diastolic volume. A pathologic fourth heart sound 326 may be heard during myocardial ischemia, in primary myocardial disease, myocardial infarction, cardiomyopathy, coronary artery disease, hypertension, aortic stenosis, and pulmonic stenosis. In association with ischemic heart disease, the fourth heart sound 326 may be loudest during episodes of angina pectoris or may occur early after an acute myocardial infarction. The fourth heart sound 326 may become fainter as a patient improves.

As with the cardiac cycle described in conjunction with FIG. 2, a cardiac cycle characteristic of myocardial ischemia includes TR segment 302 and a QT segment 304. The TR segment 302 includes a P wave 306, and complete cardiac diastole occurs during the TR segment 302.

The QT segment 304 of a cardiac cycle includes a QRS complex 308, ST segment 310, and T wave 312. As illustrated in FIG. 2, the ST segment 210 (FIG. 2) normally appears as a straight, level line between the QRS complex 208 and the T wave 212. However, as illustrated in FIG. 3, an elevated ST segment 310 (or a depressed ST segment, not illustrated) may indicate that myocardial ischemia is occurring and/or that cell necrosis is occurring or has occurred (e.g., a sign that a myocardial infarction is in process or has occurred). In addition, myocardial ischemia and/or cell necrosis may be indicated by an inverted T wave 312, when compared with a normal T wave 212 of FIG. 2.

A myocardial infarction may be classified as a STEMI (ST segment Elevated Myocardial Infarction) AMI or a non-STEMI (non-ST segment Elevated Myocardial Infarction) AMI. During a STEMI AMI, the ST segment 310 may be detected as being elevated by one or more ECG electrodes (e.g., external, subcutaneous, and/or intra-cardiac electrodes). In an embodiment, an "elevated ST segment" may be defined as an ST segment that is detected by one or more ECG electrodes to be elevated to a level at or above about 0.1 millivolts (mV). In another embodiment, an "elevated ST segment" may be defined as an ST segment that is detected by one or more ECG electrodes to be elevated to a level between a range of about 0.1 mV to about 0.2 mV. In still another embodiment, an "elevated ST segment" may be defined as an ST segment that is detected by one or more ECG electrodes to be elevated to a level at or above about 0.2 mV. In still another embodiment, an "elevated ST segment" may be defined as an ST segment that is detected by one or more ECG electrodes to be elevated to a level that may be 10% higher (or more) than the level of a baseline ST segment, where a baseline ST segment may include ECG measurements taken or accumulated over a prior period of time for a patient. In other embodiments, an "elevated ST segment" may be defined as an ST segment that is detected by one or more ECG electrodes to be elevated to levels that are different from the above-given values and/or ranges. In addition, values that indicate an elevated ST segment may be different for different types of ECG electrodes. For example, the value that indicates an elevated ST segment for an external ECG electrode may be different from (e.g., higher than or lower than) the value for a subcutaneous ECG electrode and/or an intra-cardiac electrode.

During a non-STEMI AMI, the ST segment may not appear as elevated. However, one or more ECG changes may be present. For example, the ST segment may be depressed below 0 mV, and/or the T wave may be inverted (e.g., T wave 312). In addition, a non-STEMI may be characterized by increased cardiac biomarkers, such as increased levels of cardiac troponin I and T, creatine phosphokinase, creatine phosphokinase myoglobin band, myoglobin, fatty acid binding protein, ischemia modified albumin, and/or lactic acid.

Individuals are well advised to seek medical attention during myocardial ischemia. This is particularly the case during episodes of unstable angina, non-STEMI AMI, and STEMI AMI, with STEMI AMI being the condition that may warrant the most urgent medical attention. Embodiments of the inventive subject matter provide systems, apparatus, and methods adapted to detect the onset or presence of myocardial ischemia. Various embodiments may be used for continuous or occasional heart monitoring for individuals at a high risk of having an AMI (e.g., AMI survivors, patients with previous atypical ischemic syndromes, patients that have undergone cardiac catheterization with or without the placement of a cardiac stent, patients with cardiac co-morbidities including diabetes, hypertension, metabolic syndrome, clotting blood disorders, and arrhythmias to name a few, patients with previous family history, and arrhythmia-indicated patients), and/or the various embodiments may be used in emergent situations, such as in a hospital emergency room for patients that have symptoms of myocardial ischemia or AMI.

Figure 4:
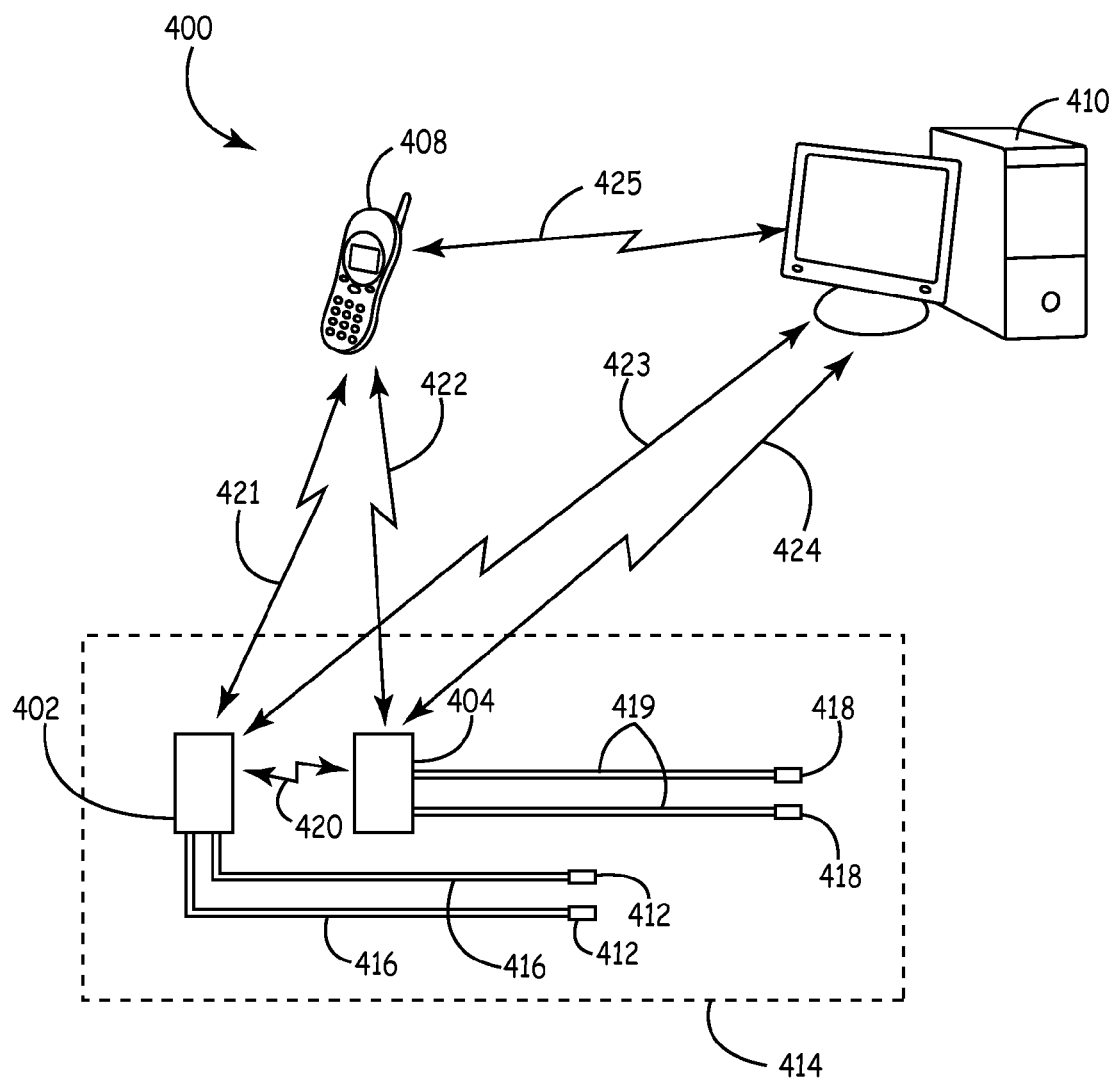
FIG. 4 illustrates a perspective view of heart monitoring system, in accordance with an example embodiment of the inventive subject matter.

FIG. 4 illustrates a perspective view of heart monitoring system 400, in accordance with an example embodiment of the inventive subject matter. System 400 may include at least one host system 402, sensing apparatus 404, patient communication device 408 (e.g., a radio, wristwatch, telephone, pager, patient activator), and computing device 410 (e.g., a computer), in an embodiment. In another embodiment, host system 402 and sensing apparatus 404 may be included within a single device. In other embodiments, some or all of host device 402, patient communication device 408, and/or computing device 410 may be excluded from the heart monitoring system 400.

In an embodiment, host system 402 and/or sensing apparatus 404 may be implanted within and/or positioned externally on a patient 414. Host system 402 may be a device adapted to provide stimuli to the heart tissue, and may include, for example but not by way of limitation, implantable pulse generator (IPG), an implantable cardiac resynchronization therapy device (CRT), implantable cardioverter defibrillator (ICD), an implantable cardiac diagnostic and monitoring device, a unit that combines two or more of the aforementioned devices, or another device. Accordingly, host system 402 may include one or more stimulus elements (e.g., electrical and/or mechanical stimulus elements) 412 adapted to be implanted within a patient 414. The stimulus elements 412 may be coupled to host system 402 via leads 416, or they may have leadless (e.g., direct, wireless radio frequency, and/or ultrasound) connections to host system 402 and/or to each other. Leads 416 may include transvenous leads and/or subcutaneous tethers, in various embodiments.

Sensing apparatus 404 may include an apparatus adapted to sense one or more vibratory, mechanical, electrical, magnetic, chemical, radiant, thermal or patient-initiated activity. As used herein, the terms "sensor" and "sensing apparatus" may be used interchangeably. In an embodiment, sensing apparatus 404 may include one or more sensing elements 418 adapted to be implanted within or positioned externally to patient 414. The sensing elements 418 may be coupled to sensing apparatus 404 via leads 419, or they may have leadless (e.g., direct, wireless radio frequency, and/or ultrasound) connections to sensing apparatus 404 and/or to each other. Leads 419 may include transvenous leads and/or subcutaneous tethers, in various embodiments. Leads 416 and 419 may be the same or different leads, in various embodiments. A sensing element 418 may include, for example but not by way of limitation, a microphone, accelerometer, resonator, voltage or current detector, hall sensor, blood collection device, oxygen sensor, and/or temperature sensor. In an embodiment, a sensing element 418 also or alternatively may include a patient activator, which enables a patient manually to indicate the presence of a symptom. For example, when a patient feels one or more symptoms that are associated with cardiac ischemia, the patient may activate the patient activator in response to the symptoms. In an embodiment, a patient activator may have inputs adapted to enable the patient to indicate the type of symptom, as well. For example, a first input may indicate acute pectoral angina (i.e., chest pain), a second input may indicate shortness of breath, and a third input may indicate fatigue, for example. In an embodiment, different inputs may cause a different response in system 400.

Sensing apparatus 404 may further include apparatus adapted to produce information representing the sensed activity over time, in an embodiment. For example, but not by way of limitation, sensor-produced information may include a sound waveform (e.g., sound waveforms 218, 318, FIGS. 2 and 3), a vibration waveform, an ECG waveform (e.g., ECG waveforms 200, 300, FIGS. 2 and 3), a magnetic magnitude waveform, a biomarker level waveform, an oxygen level waveform, a body temperature waveform, and or patient activator input signals (e.g., symptomatic or asymptomatic, type of symptom, etc.), or other sensor-produced information. Sensing apparatus 404 may further include apparatus adapted to analyze sensed activity, and to produce an output signal based on the analysis. Output signals may include, for example, analog or digital signals indicating values of the sensed activity, and or signals indicating that a sensed activity has reached or exceeded a threshold (or fallen below a threshold), for example.

In an embodiment, when host system 402 and sensing apparatus 404 are discrete devices, they may communicate with each other over wireless intrabody link 420. In addition, in various embodiments, either or both host system 402 and/or monitor device 404 may communicate with patient communication device 408 and external system communication device 410 over wireless extrabody links 421, 422, 423, 424. Additionally, patient communication device 408 and computing device 410 may communicate with each other over wireless device-to-device link 425. A variety of different wireless communication technologies may be used to support communication over links 420-425.

During operation, system 400 may function to sense various activity, and to produce signals representing the sensed activity, via sensing apparatus 404 and/or host system 402. The sensed activity signals may be communicated with other system elements. Host system 402 and/or the various system elements may (or may not) take action based on the sensed activity signals. An example of system 400 operation is given below. The example is not meant to limit the scope of the inventive subject matter.

In one operational scenario, sensing apparatus 404 may be adapted to sense one or more cardiac activities. For example, sensing apparatus 404 may include one or more voltage sensors, which may be positioned proximate to one or more areas of the heart in order to sense bioelectrical stimulation of the heart. Also, sensing apparatus 404 may include one or more mechanical sensors (e.g., microphones, accelerometers, pressure sensors, heart wall motion sensors, or resonators), which also may be positioned proximate to one or more areas of the heart in order to sense mechanical cardiac activity (e.g., heart sounds and/or vibration of the heart walls). Sensing apparatus 404 may include one or more additional sensors to sense other activities, in various embodiments. Sensing apparatus 404 may convert the sensed bioelectrical stimuli, mechanical cardiac activity, and other sensed stimuli, if any, into signals that may be further analyzed by sensing apparatus 404, host system 402 or another system component. When host system 402 or another system component is adapted to analyze the signals, sensing apparatus 404 may transmit the signals over one or more of intrabody link 420 and/or extrabody links 421-422.

Signal analysis, which may be performed by sensing apparatus 404, host system 402, and/or another system component, may include analyzing the signals to determine whether a likelihood exists that myocardial ischemia is occurring. In addition, signal analysis may include considering other factors, such as whether a patient has indicated (e.g., via patient communication device 408) that the patient is experiencing angina (e.g., acute angina pectoris). Signal analysis is described in more detail in conjunction with FIGS. 5 and 6, later.

In an embodiment, when a likelihood exists that myocardial ischemia is occurring, one or more of the system components may take further action. For example, host system 402 may produce a stimulus to the heart tissue (e.g., defibrillation stimulus, pacing stimulus, pacing rate adjustment, pacing characteristic adjustment, and/or pulse adjustment stimulus). In addition or alternatively, patient communication device 408 and/or computing device 410 may produce an audible, visual or mechanical alert, and/or may provide instructions to the patient via a display or speaker. Instructions may include, for example, instructions to reduce activity, change posture or position, take a blood sample and perform a biomarker test, and/or seek medical attention. A patient's current activity, workload, posture, and/or position may be determined by one or more accelerometers, heart rate sensors, pulse sensors, pressure sensors, or other sensors included within system 400. In an embodiment, for example, system 400 may include a multi-axis accelerometer, which may be used to identify various postures (e.g., sitting or supine). Because posture may affect the amplitudes of heart sounds, this information may be used, for example, to normalize baseline heart sound information and/or to adjust heart sound thresholds, as will be discussed later. In other embodiments, heart rate, pulse pressure, and/or changes in pressure with time may be used to normalize baseline information and/or to adjust thresholds.

Patient communication device 408 and/or computing device 410 additionally or alternatively may connect over an external system to convey information regarding the patient to a remote individual or system. For example, patient communication device 408 and/or computing device 410 may connect over a cellular, radio, telephone, or computer network with a doctor's office, emergency response system (e.g., a 911 system), hospital, caretaker or other entity to indicate the likelihood of the myocardial ischemia. In addition, data representing the sensed stimuli may be conveyed over the external system. The remote individual or system may be able to communicate with the patient via patient communication device 408 and/or computing device 410.

In an embodiment, a likelihood that myocardial ischemia is occurring is determined by a myocardial ischemia detection apparatus. A myocardial ischemia detection apparatus may be included within sensing apparatus 404 and/or host system 402, in various embodiments. In other embodiments, some portions of a myocardial ischemia detection apparatus may be included within another system component (e.g., patient communication device 408 and/or computing device 410), or portions of a myocardial ischemia detection apparatus may be distributed across multiple system components.

Figure 5:
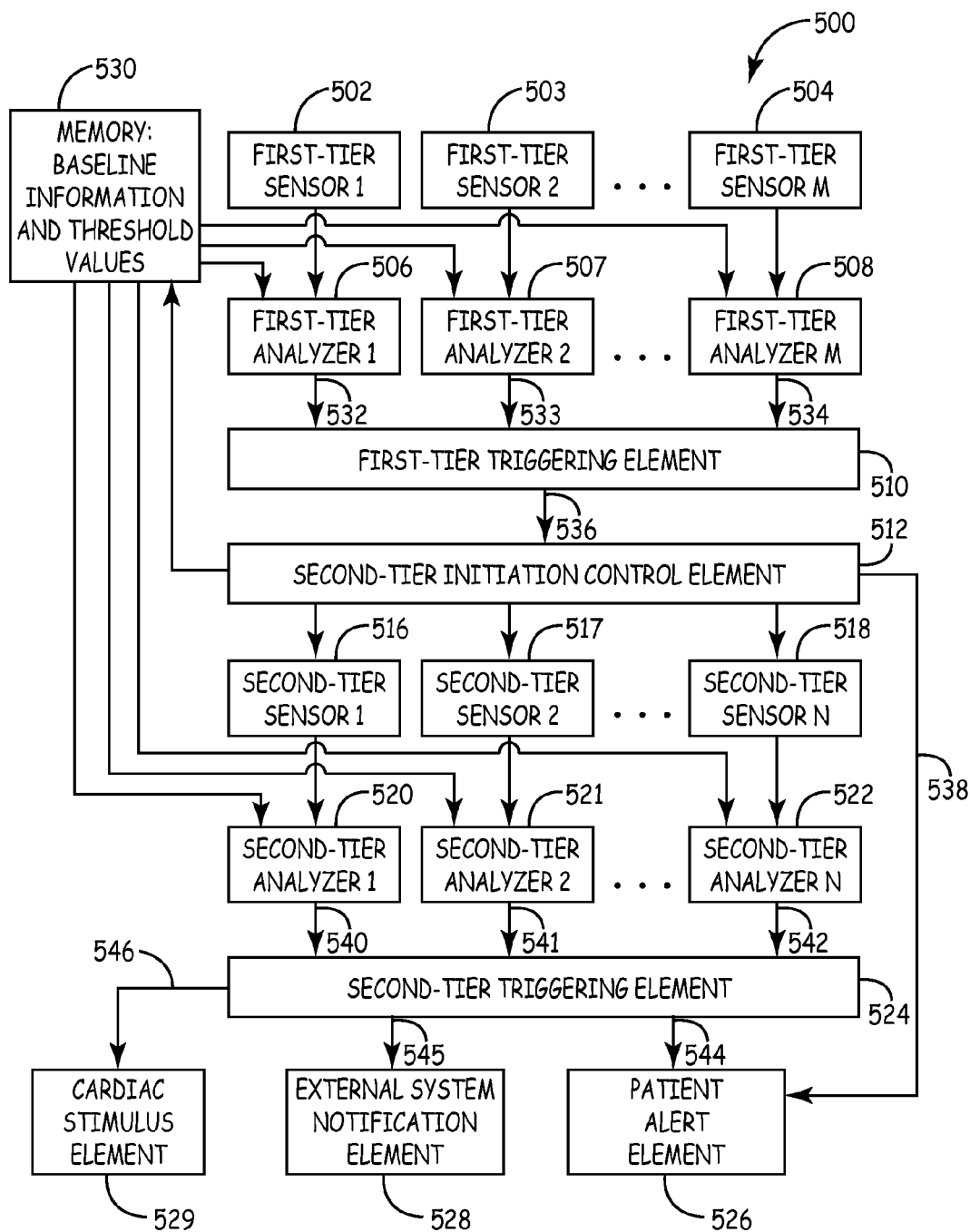
FIG. 5 illustrates a functional block diagram of a myocardial ischemia detection apparatus, in accordance with an example embodiment.

FIG. 5 illustrates a functional block diagram of a myocardial ischemia detection apparatus 500, in accordance with an example embodiment. In various embodiments, the elements of apparatus 500 may be located in a single device package (e.g., host system 402 or sensing apparatus 404, FIG. 4), or may be distributed among multiple device packages. Additionally, interconnections between the various elements of apparatus 500 may be direct, wired or wireless, in various embodiments.

Apparatus 500 may include at least one first-tier sensor 502, 503, 504, at least one first-tier analyzer 506, 507, 508, and a first-tier triggering element 510, in an embodiment. In addition, in an embodiment, apparatus 500 may include a second-tier initiation control element 512, at least one second-tier sensor 516, 517, 518, at least one second-tier analyzer 520, 521, 522, a second-tier triggering element 524, a patient alert element 526, an external system notification element 528, and a cardiac stimulus element 530. Apparatus 500 also includes memory 530, which may include one or more memory elements (e.g., random access memory (RAM), read-only memory (ROM), or other memory element). Memory 530 is adapted to store baseline information and/or threshold values, in an embodiment. FIG. 5 illustrates M first-tier sensors 502-504 and first-tier analyzers 506-508, where M may be any integer value from 1 to 10. FIG. 5 also illustrates N second-tier sensors 516-518 and second-tier analyzers 520-522, where N may be any integer value from 1 to 10. When referred to together, a sensor (e.g., sensor 502) and an analyzer (e.g., analyzer 506) may be termed a "sensor/analyzer."

Each first-tier sensor/analyzer 502-504, 506-508 is adapted to sense an input related to cardiac function, and to produce a first-tier trigger signal 532-534 when the input indicates myocardial ischemia. In an embodiment, one of first-tier sensors (e.g., sensor 502) includes a set of ECG sensors, and a corresponding one of first-tier analyzers (e.g., analyzer 506) includes ECG waveform processing electronics. Accordingly, first-tier sensor 502 may be referred to herein as "ECG sensor 502," and first-tier analyzer 506 may be referred to herein as "ECG analyzer 506." Collectively, they may be referred to herein as an "ECG sensor/analyzer."

ECG sensor 502 may include, for example, a set of leads (e.g., 12 leads) that provide connections between a package (e.g., host system 402 or sensing apparatus 404, FIG. 4) and sensors (e.g., electrodes) placed at various locations in proximity to a heart. In another embodiment, ECG sensor 502 may include leadless sensors, which are directly coupled to a package. In an embodiment, ECG sensor 502 and ECG analyzer 506 are continuously active, meaning that ECG sensor 502 continuously senses bioelectrical activity, and ECG analyzer 506 continuously produces a corresponding ECG waveform. In an alternate embodiment, ECG sensor 502 and/or ECG analyzer 506 may be activated periodically or occasionally as a result of some trigger condition.

In an embodiment, ECG analyzer 506 receives baseline information and/or one or more threshold values from memory 530. Baseline information may include, for example, baseline ECG information, which includes data representing ECG waveforms for one or more previous cardiac cycles. The baseline ECG information may include several sets of baseline information, including for example, baseline information representing ECG waveforms previously produced during periods of rest and/or activity, at different points in a respiration cycle, at various heart rates, at different body temperatures, and/or while the patient was positioned in various postural positions (e.g., sitting, supine and/or other). Desirably, the baseline ECG information represents ECG waveforms produced while the patient was not encountering myocardial ischemia.

ECG analyzer 506 produces a current ECG waveform from bioelectrical activity sensed by ECG sensor 502, and compares the current ECG waveform to the baseline ECG information retrieved from memory 530. In an embodiment, ECG analyzer 506 may select a particular set of baseline ECG information based on the patient's level of activity, the point in the respiration cycle, heart rate, and/or posture, among other things. In another embodiment, a single set of baseline ECG information may be stored in memory 530, and such a selection may not be performed. Comparison of the current ECG waveform and the baseline ECG information may include performing a correlation algorithm, in an embodiment, which may compensate for timing delays and pacing differences between the current ECG waveform and the baseline ECG information. ECG analyzer 506 may produce a comparison result, in an embodiment, which indicates differences between the current ECG waveform and the baseline ECG information.

ECG analyzer 506 may additionally determine whether the comparison result has reached or exceeded a threshold, referred to herein as an "ECG result threshold," which may indicate that myocardial ischemia is occurring. An ECG result threshold may indicate a difference value between corresponding portions of the current ECG waveform and the baseline ECG information. In an embodiment, for example, a particular surface ECG result threshold may be a difference of 0.1 mV or more between a baseline ST segment (e.g., ST segment 210, FIG. 2) and a current ST segment (e.g., ST segment 310, FIG. 3). In another embodiment, a surface ECG result threshold may be a difference of −0.1 mV or more between a baseline T wave (e.g., T wave 212, FIG. 2) and a current T wave (e.g., T wave 312, FIG. 3). In an embodiment, when an ECG result threshold is reached or exceeded, then ECG analyzer 506 produces an ECG trigger signal 532. Processing of the ECG trigger signal 532 will be discussed later.

In the embodiments discussed above, an ECG trigger signal 532 is produced based on whether a comparison of a current ECG waveform and baseline ECG information yields a comparison result that exceeds one or more ECG result thresholds. In an alternate embodiment, a current ECG waveform may be compared directly to one or more ECG result thresholds. Accordingly, one or more portions of a current ECG waveform may be analyzed to determine, for example, whether voltages during those portions meet, exceed, or are less than one or more ECG result thresholds. For example, a determination may be made whether the voltage for a current ST segment (e.g., ST segment 310, FIG. 3) is equal to or greater than an ST segment threshold (e.g., 0.1 mV or some other threshold). As another example, a determination may be made whether a T wave (e.g., T wave 312, FIG. 3) is below 0 mV (i.e., the T wave is inverted). In an embodiment, when an ECG result threshold is reached or exceeded, then ECG analyzer 506 produces an ECG trigger signal 532. Again, processing of the ECG trigger signal 532 will be discussed later.

In an embodiment, an ECG sensor 502 and an ECG analyzer 506 are the only first-tier sensor and first-tier analyzer included in system 500. In other embodiments, one or more additional first-tier sensors 503-504 and first-tier analyzers 507-508 may be included in system 500. For example, but not by way of limitation, the one or more additional first-tier sensors 503-504 and first-tier analyzers 507-508 may include any combination of one or more sensors/analyzers adapted to sense and analyze one or more vibratory, mechanical, electrical, magnetic, chemical, radiant, thermal or patient-initiated activity (e.g., a patient indicating the presence of symptoms through a user interface of a patient activator).

In a particular embodiment, an additional first-tier sensor (e.g., sensor 503) includes one or more vibration sensors (e.g., a heart sound sensors), and a corresponding additional first-tier analyzer (e.g., analyzer 507) includes vibration processing electronics (e.g., heart sound analysis electronics). Accordingly, first-tier sensor 503 may be referred to herein as "heart sound sensor 503," and first-tier analyzer 507 may be referred to herein as "heart sound analyzer 507." Collectively, they may be referred to herein as a "heart sound sensor/analyzer."

Heart sound sensor 503 may include, for example, a set of leads that provide connections between a package (e.g., host system 402 or sensing apparatus 404, FIG. 4) and sensors placed at various locations in proximity to a heart. Sensors may include, for example but not by way of limitation, any combination of one or more microphones, accelerometers, and/or resonators. In another embodiment, heart sound sensor 503 may include leadless sensors, which are directly coupled to a package. In an embodiment, heart sound sensor 503 and heart sound analyzer 507 are continuously active, meaning that heart sound sensor 502 continuously senses vibratory cardiac activity, and heart sound analyzer 507 continuously produces a corresponding sound wave. In an alternate embodiment, heart sound sensor 503 and/or heart sound analyzer 507 may be activated periodically or occasionally. For example, in an embodiment, heart sound sensor 503 and/or heart sound analyzer 507 may be activated during certain portions of a cardiac cycle, such as during those portions when a first heart sound (e.g., heart sound 320, FIG. 3), a second heart sound (e.g., heart sound 322), a third heart sound (e.g., heart sound 324), and/or a fourth heart sound (e.g., heart sound 326) may occur. Occasional activation of heart sound sensor 503 and/or heart sound analyzer 507 may help to conserve power.

In an embodiment, heart sound analyzer 507 receives baseline information and/or one or more threshold values from memory 530. Baseline information may include, for example, baseline heart sound information, which includes data representing heart sound waveforms for one or more previous cardiac cycles. The baseline heart sound information may include several sets of baseline information, including for example, baseline information representing heart sound waveforms previously produced during periods of rest and/or activity, at different points in a respiration cycle, at various heart rates, at different body temperatures, and/or while the patient was positioned in various postural positions (e.g., sitting, supine and/or other). Desirably, the baseline heart sound information represents heart sound waveforms produced while the patient was not encountering myocardial ischemia.

Heart sound analyzer 507 produces a current heart sound waveform from vibratory cardiac activity sensed by heart sound sensor 503, and compares the current heart sound signal to the baseline heart sound information retrieved from memory 530. In an embodiment, heart sound analyzer 507 may select a particular set of baseline heart sound information based on the patient's level of activity, the point in the respiration cycle, heart rate, and/or posture, among other things. In another embodiment, a single set of baseline heart sound information may be stored in memory 530, and such a selection may not be performed. Comparison of the current heart sound signal and the baseline heart sound information may include performing a correlation algorithm, in an embodiment, which may compensate for timing delays and pacing differences between the current heart sound signal and the baseline heart sound information. In addition, heart sound analyzer 507 may receive current ECG waveforms and/or trigger information that enable heart sound analyzer 507 to determine where, within a cardiac cycle, various sensed heart sounds are occurring. In an embodiment, a first heart sound (e.g., heart sound 320, FIG. 3) may be used as a reference, as it generally has the greatest amplitude of all of the heart sounds. Heart sound analyzer 507 may produce a comparison result, in an embodiment, which indicates differences between the current heart sound signal and the baseline heart sound information. A comparison result may include difference information for one or more heart sounds (e.g., S1, S2, S3, and/or S4). In an embodiment, difference information for a fourth heart sound (S4) is particularly represented as the new appearance and/or change in amplitude of a fourth heart sound, which may indicate current myocardial ischemia.

Heart sound analyzer 507 may additionally determine whether the comparison result has reached or exceeded a threshold for a particular heart sound, referred to herein as a "heart sound result threshold," which may indicate that myocardial ischemia is occurring. In a particular embodiment, heart sound analyzer 507 determines whether difference information for a fourth heart sound has reached or exceeded a fourth heart sound result threshold during a relatively short period of time. A heart sound result threshold may indicate a difference value between corresponding portions of the current heart sound waveform and the baseline heart sound information. In an embodiment, for example, when a fourth heart sound (e.g., fourth heart sound 326, FIG. 3) was previously undetectable, a heart sound result threshold for the fourth heart sound may have a value of about 10% (or more) of the amplitude of the first heart sound (e.g., first heart sound 320), although higher or lower thresholds alternatively could be used. In another embodiment, when a fourth heart sound was previously detectable at a steady-state amplitude, a heart sound result threshold for the fourth heart sound may have a value of about 200% of the steady-state amplitude, although higher or lower thresholds alternatively could be used. In another embodiment, when a third heart sound (e.g., heart sound 324) was previously undetectable, a heart sound result threshold for the third heart sound may have a value of about 10% (or more) of the amplitude of the first heart sound (e.g., first heart sound 320), although higher or lower thresholds alternatively could be used. In another embodiment, when a third heart sound was previously detectable at a steady-state amplitude, a heart sound result threshold for the third heart sound may have a value of about 200% of the steady-state amplitude, although higher or lower thresholds alternatively could be used. In an embodiment, when a heart sound result threshold is reached or exceeded, then heart sound analyzer 507 produces a heart sound trigger signal 533. In an embodiment, one or more heart sound result thresholds (e.g., for the third heart sound and/or the fourth heart sound) may be programmable percentages within a range. In some cases, the detection of the fourth heart sound (or third heart sound) will be an input; in other cases it will be a threshold increase in the amplitude of the fourth heart sound (or third heart sound). Processing of the heart sound trigger signal 533 will be discussed later.

In the embodiments discussed above, a heart sound trigger signal 533 is produced based on whether a comparison of a current heart sound waveform and baseline heart sound information yields a comparison result that exceeds one or more heart sound result thresholds. In an alternate embodiment, a current heart sound waveform may be compared directly to one or more heart sound result thresholds. Accordingly, one or more portions of a current heart sound waveform may be analyzed to determine, for example, whether sound sensed during those portions meet, exceed, or are less than one or more heart sound result thresholds. For example, a determination may be made whether a current fourth heart sound has an amplitude equal to or greater than a fourth heart sound threshold (e.g., 10% of the amplitude of the first heart sound, or some other threshold). As another example, a determination may be made whether a current third heart sound has an amplitude equal to or greater than a third heart sound threshold (e.g., 10% of the amplitude of the first heart sound or some other threshold). In an embodiment, when a heart sound result threshold is reached or exceeded, then heart sound analyzer 507 produces a heart sound trigger signal 533. Again, processing of the heart sound trigger signal 533 will be discussed later.

In other embodiments, one or more additional first-tier sensors (e.g., sensor 504) may be included in system 500, such as a vibration sensor, a pressure sensor, a change in pressure with time (dp/dt) sensor, a magnetic sensor, a hall sensor, a blood collection device and biomarker level sensor, an oxygen level sensor, carbon dioxide level sensor, a glucose sensor, a pH sensor, a temperature sensor, a heart rate sensor, a heart rate variability sensor, a heart wall motion sensor, an impedance sensor, an optical sensor, a respiration sensor, and/or a patient activator. In addition, one or more corresponding additional first-tier analyzers (e.g., analyzer 508) may be included in system 500. The one or more additional first-tier analyzers (e.g., analyzer 508) may analyze sensor signals by comparing the sensor signals to corresponding baseline information and/or to corresponding threshold values. When a sensor signal meets or exceeds a threshold value, an additional first-tier sensor (e.g., sensor 504) may produce a first-tier trigger signal (e.g., trigger signal 534).

First-tier triggering element 510 receives one or more of first-tier trigger signals 532-534 from one or more of first-tier analyzers 502-504. In an embodiment, first-tier triggering element 510 includes logical OR circuitry, which produces a second-tier initiation signal 536 when any one or more of first-tier trigger signals 532-534 indicate a trigger condition. In another embodiment, first-tier triggering element 510 may include logical AND circuitry, which produces a second-tier initiation signal 536 when more than one and/or all of first-tier trigger signals 532-534 indicate trigger conditions. In still another embodiment, in which only one first-tier sensor (e.g., sensor 502) and first-tier analyzer (e.g., analyzer 506) is included within system 500, first-tier triggering element 510 may be excluded.

Second-tier initiation control element 512 (also referred to herein as a "control element") is adapted to activate inactivated ones of the at least one second-tier sensor/analyzer when at least one first-tier trigger signal (e.g., one or more of first-tier trigger signals 532-534) is produced, and/or when a second-tier initiation signal 536 is produced. In an embodiment, second-tier initiation control element 512 receives the second-tier initiation signal 536 (or a first-tier trigger signal 532-534 from a first-tier analyzer 506-508, when first-tier triggering element 510 is excluded). In response to the second-tier initiation signal 536, second-tier initiation control element 512 may take any one or more of several possible actions. In an embodiment, for example, second-tier initiation control element 512 may produce an alert signal 538 indicating that myocardial ischemia may have been detected.

Patient alert element 526 is adapted to receive alert signal 538, and to provide an alert to the patient. For example, but not by way of limitation, patient alert element 526 may produce an audible or vibratory alert. In addition or alternatively, patent alert block 526 may produce an audible or displayed message, indicating to the patient that they should take some action. Such actions may include, for example but not by way of limitation, instructions to reduce activity, change posture or position, take a blood sample and perform a biomarker test, and/or seek medical attention. Patient alert element 526 also may be invoked, in an embodiment, to instruct the patient to take some action (e.g., reduce activity and/or change posture or position) when a signal-to-noise ratio (SNR) of one or more of first-tier sensors/analyzers or second-tier sensors/analyzers is lower than an SNR threshold. In an embodiment, system 500 may include one or more mechanical sensors (e.g., microphones, accelerometers, resonators, pressure sensors, heart wall motions sensors, or other mechanical sensors, not illustrated) that may be placed in one or more positions that are relatively insensitive to heart sounds, but that are likely to sense noise due to exterior mechanical interactions. Inputs from such sensors may be used to eliminate exterior mechanical sounds, and to increase the SNR for heart sound sensing/analysis.

In an embodiment, second-tier initiation control element 512 also may activate one or more second-tier sensors 516-518 and second-tier analyzers 520-522. Each second-tier sensor/analyzer 516-518, 520-522 is adapted to sense an input related to cardiac function, and to produce a second-tier trigger signal 540-542 when the input indicates myocardial ischemia. Second-tier sensors 516-518 and second-tier analyzers 520-522 may include, for example but not by way of limitation, any combination of one or more sensors/analyzers adapted to sense and analyze one or more vibratory, mechanical, electrical, magnetic, chemical, radiant, thermal or patient-initiated activity. In an embodiment, some or all of second-tier sensors 516-518 and second-tier analyzers 520-522 may be the same as first-tier sensors 502-504 and first-tier analyzers 506-508, in which cases the hardware and circuitry may not be duplicated, and activation may not be performed.

In an embodiment, second-tier initiation control element 512 may adjust threshold values stored in memory 530 for those analyzers that are present in the first-tier and/or the second-tier. For example, second-tier initiation control element 512 may adjust threshold values so that the second-tier analyzers 520-522 are more sensitive (e.g., reduce the threshold values). In an alternate embodiment, second-tier analyzers 520-522 may use different threshold values from those used previously. Thresholds may also be adjusted at other times and/or in other ways (e.g., in response to historical data and/or external inputs).

Similar to the functioning of first-tier analyzers 506-508, second-tier analyzers 520-522 may receive and process signals from second-tier sensors 516-518, and may compare the processed signals to baseline information retrieved from memory 530. In addition or alternatively, second-tier analyzers 520-522 may determine whether comparison results, signals or waveforms based on the second-tier sensor 516-518 outputs meet or exceed corresponding threshold values (or adjusted threshold values). When a comparison result, signal or waveform does meet or exceed a corresponding threshold value (or adjusted threshold value), a second-tier analyzer 520-522 may produce a second-tier trigger signal 540, 541, 542.

Second-tier triggering element 524 receives the one or more second-tier trigger signals 540-542 from the one or more second-tier analyzers 520-522. In an embodiment, second-tier triggering element 524 includes logical OR circuitry, which produces one or more response-invoking signals 544, 545, 546 when any one or more of second-tier trigger signals 540-542 indicate a trigger condition. In another embodiment, second-tier triggering element 524 may include logical AND circuitry, which produces one or more response-invoking signals 544-546 when more than one and/or all of second-tier trigger signals 540-542 indicate trigger conditions. In still another embodiment, in which only one second-tier sensor (e.g., sensor 516) and second-tier analyzer (e.g., analyzer 520) is included within system 500, second-tier triggering element 524 may be excluded.

Response-invoking signals 544-546 may be received by any one or more of patient alert element 526, external system notification element 528, and cardiac stimulus element 529. In an embodiment, when patient alert element 526 receives a response-invoking signal 544 indicating that myocardial ischemia may be occurring, patient alert element 526 may respond by providing an alert to the patient. For example, as discussed previously, patient alert element 526 may produce an audible or vibratory alert or an audible or displayed message, indicating to the patient that they should take some action. The patient alert may be different from the previous alert, if one previously was produced. For example, the patient alert may indicate that more urgent action should be performed, such as an alert to contact emergency medical personnel immediately.

In an embodiment, external system notification element 526 also or alternatively may receive a response-invoking signal 545. In response, external system notification element 526 may send a signal or message to a patient communication device (e.g., device 408, FIG. 4) or a computing device (e.g., device 410, FIG. 4) indicating that myocardial ischemia may be occurring. As discussed previously, a patient communication device (e.g., device 408, FIG. 4) and/or a computing device (e.g., device 410, FIG. 4) may connect over an external system to convey information regarding the patient to a remote individual or system. In addition, data representing the sensed stimuli may be conveyed over the external system.

In an embodiment, cardiac stimulus element 529 also or alternatively may receive a response-invoking signal 546. In response, cardiac stimulus element 529 may produce a stimulus to the heart tissue (e.g., defibrillation stimulus, pacing stimulus, pacing rate adjustment, pacing characteristic adjustment, and/or pulse adjustment stimulus).

The functional block diagram of FIG. 5 may be implemented in hardware in any of a number of ways. In particular, some or all of the various elements may be implemented using one or more processors, memory elements, logical processing blocks, and other hardware. Additionally, the various elements may be implemented in software, hardware, or both. Further, some or all of the various elements may be implemented on the same hardware platform, on different hardware platforms, using the same processor/hardware, and/or using different processors/hardware.

As discussed previously, various embodiments may include various numbers of first-tier sensors/analyzers and second-tier sensors/analyzers. In a particular embodiment, only an ECG sensor and an ECG analyzer are included as a first-tier sensor/analyzer, and at least one different type of sensor/analyzer are included in the second-tier sensors/analyzers. In particular, at least a heart sound sensor/analyzer is included as a second-tier analyzer. Such a system may have relatively high specificity, meaning that the system may be adapted to produce an alarm, external system notification, and/or cardiac stimulus at relatively low first-tier and second-tier thresholds than other embodiments, as both thresholds are crossed in order to generate a patient alert. Method embodiments for such systems are discussed below, in conjunction with FIG. 6.

Figure 6:
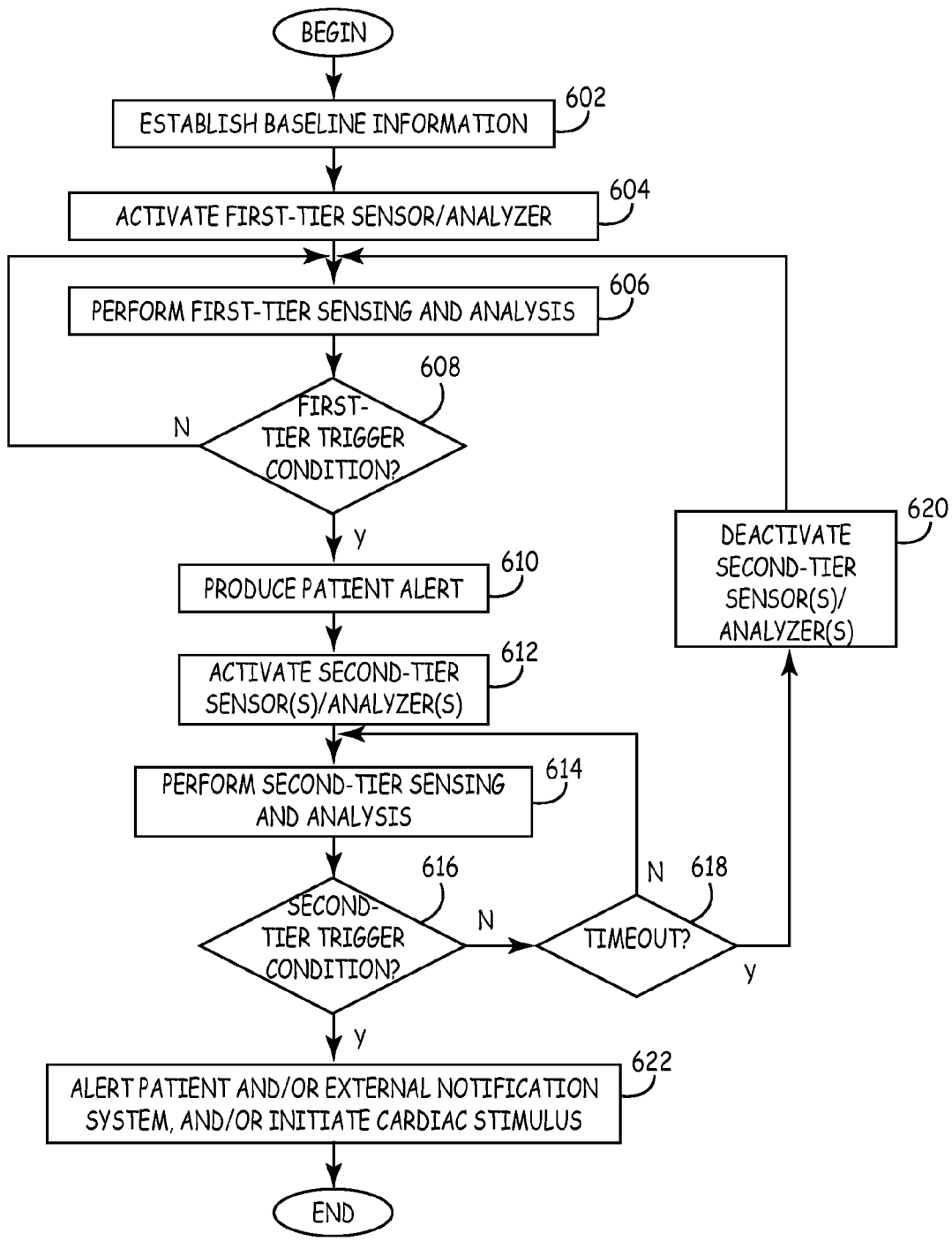
FIG. 6 illustrates a flowchart of a method for detecting myocardial ischemia, in accordance with an example embodiment.

FIG. 6 illustrates a flowchart of a method for detecting myocardial ischemia, in accordance with an example embodiment. The method begins, in an embodiment, by establishing baseline information for the patient, in block 602. Establishing baseline information may include, for example, collecting and storing data representing ECG waveforms and heart sounds, among other things, for one or more cardiac cycles. As discussed previously, the baseline information may include several sets of baseline information, including for example, baseline information representing signals or waveforms produced during periods of rest and/or activity, at different points in a respiration cycle, at various heart rates, at different body temperatures, and/or while the patient was positioned in various postural positions (e.g., sitting, supine and/or other). Desirably, the baseline information represents signals or waveforms produced while the patient was not encountering myocardial ischemia. Establishing baseline information may be performed one time, periodically, or continuously (as long as myocardial ischemia is not occurring), in various embodiments.

Unless already activated, a first-tier sensor/analyzer (e.g., first-tier sensor 502 and analyzer 506, FIG. 5) may be activated, in block 604. In an embodiment, the first-tier sensor/analyzer includes an ECG sensor/analyzer. In an alternate embodiment, a first-tier sensor/analyzer includes another type of sensor/analyzer, such as a heart sound sensor/analyzer, vibration sensor/analyzer, pressure sensor/analyzer, change in pressure with time (dp/dt) sensor/analyzer, magnetic sensor/analyzer, hall sensor/analyzer, biomarker level sensor/analyzer, oxygen level sensor/analyzer, carbon dioxide level sensor/analyzer, glucose sensor/analyzer, pH sensor/analyzer, body temperature sensor/analyzer, heart rate sensor/analyzer, heart rate variability sensor/analyzer, heart wall motion sensor/analyzer, impedance sensor/analyzer, optical sensor/analyzer, respiration sensor/analyzer, and/or a patient activator, for example.

In block 606, first-tier sensing and analysis is performed, as was discussed previously in conjunction with elements 502-504 and 506-508 of FIG. 5. For example, in an embodiment, first-tier sensing and analysis may include taking ECG readings, producing a current ECG waveform, comparing the current ECG waveform to baseline ECG information, and determining whether the difference between the current ECG waveform and the baseline ECG information meets or exceeds a threshold. In another embodiment, first-tier sensing and analysis may include taking ECG readings, producing a current ECG waveform, and determining whether one or more portions of the ECG waveform (e.g., an ST segment 210 or 310, FIG. 2 or 3) meet or exceed a threshold. When the difference between the current ECG waveform and the baseline ECG information meets or exceeds a threshold, or when one or more portions of the ECG waveform meet or exceed a threshold, a positive trigger signal (e.g., trigger signal 532, FIG. 5) may be produced. In other embodiments, where a different type of sensor/analyzer is used as the first-tier sensor/analyzer, a different type of sensing and analysis would be performed.

In block 608, a determination is made whether a first-tier trigger condition has occurred. In an embodiment, a first-tier trigger condition has occurred when a positive trigger signal is produced by an ECG sensor/analyzer, as discussed above. When a first-tier trigger condition has not occurred, the method iterates as shown. When a first-tier trigger condition has occurred, then a patient alert may be produced, in block 610. As discussed previously in conjunction with block 526 (FIG. 5), a patient alert may include an audible or vibratory alert, and/or an audible or displayed message. In an alternate embodiment, a patient alert may not be produced at this point.

In block 612, one or more second-tier sensors/analyzers may be activated. In an embodiment, the one or more second-tier sensors/analyzers include at least a heart sound sensor/analyzer. The one or more second-tier sensors/analyzers may also include an ECG sensor/analyzer, vibration sensor/analyzer, pressure sensor/analyzer, change in pressure with time (dp/dt) sensor/analyzer, magnetic sensor/analyzer, hall sensor/analyzer, biomarker level sensor/analyzer, oxygen level sensor/analyzer, carbon dioxide level sensor/analyzer, glucose sensor/analyzer, pH sensor/analyzer, body temperature sensor/analyzer, heart rate sensor/analyzer, heart rate variability sensor/analyzer, heart wall motion sensor/analyzer, impedance sensor/analyzer, optical sensor/analyzer, respiration sensor/analyzer, and/or a patient activator, for example.

In block 614, second-tier sensing and analysis is performed, as was discussed previously in conjunction with elements 516-518 and 520-522 of FIG. 5. For example, in an embodiment, second-tier sensing and analysis may include taking heart sound readings, producing a current heart sound waveform, comparing the current heart sound waveform to baseline heart sound information, and determining whether the difference between the current heart sound waveform and the baseline heart sound information meets or exceeds a threshold. In another embodiment, second-tier sensing and analysis may include taking heart sound readings, producing a current heart sound waveform, and determining whether a third heart sound (e.g., heart sound 324, FIG. 3) and/or a fourth heart sound (e.g., heart sound 326, FIG. 3) are present to an extent that they meet or exceed a threshold. When a third heart sound and/or a fourth heart sound are present to an extent that they meet or exceed a threshold, a positive trigger signal (e.g., trigger signal 540, FIG. 5) may be produced. In other embodiments, where one or more different types of sensor/analyzers are used as the second-tier sensors/analyzers, different types of sensing and analysis would be performed.

In block 616, a determination is made whether a second-tier trigger condition has occurred. In an embodiment, a second-tier trigger condition has occurred when a positive trigger signal is produced by a second-tier sensor/analyzer (e.g., a heart sound sensor/analyzer), as discussed above. When a second-tier trigger condition has not occurred, a determination is made whether a second-tier sensing timeout has occurred, in block 618. A second-tier sensing timeout may be on the order of minutes to hours, in an embodiment. When a second-tier sensing timeout has not occurred, the method continues to perform second-tier sensing/analysis, as shown. When a second-tier sensing timeout has occurred, the second-tier sensors/analyzers may be deactivated, in block 620, and the method returns to performing first-tier sensing/analysis, as shown.

Referring again to block 616, when a second-tier trigger condition has occurred, then a patient alert may be produced, an external notification system may be contacted, and/or a cardiac stimulus may be initiated, in block 622. As discussed previously in conjunction with blocks 526, 528, and 529 (FIG. 5), a patient alert may include an audible or vibratory alert, and/or an audible or displayed message. Contacting an external notification system may include sending a message to a patient communication device (e.g., device 408, FIG. 4) or a computing device (e.g., device 410, FIG. 4) indicating that myocardial ischemia may be occurring. Initiating a cardiac stimulus may include producing a stimulus to the heart tissue (e.g., defibrillation stimulus, pacing stimulus, pacing rate adjustment, pacing characteristic adjustment, and/or pulse adjustment stimulus). The method may then end.

The method illustrated in FIG. 6 pertains to embodiments of a system in which a single first-tier sensor/analyzer is included. In other embodiments, a plurality of first-tier sensors/analyzers may be included within a system. In a particular embodiment, at least an ECG sensor/analyzer and a heart sound sensor/analyzer may be present as first-tier sensors/analyzers. One or more different types of sensors/analyzers also may be present as first-tier sensors/analyzers. The ECG sensor/analyzer and the heart sound sensor/analyzer (and/or the other sensors/analyzers, if any) also may be present as second-tier sensors/analyzers. In such an embodiment, the comparison threshold values may be higher (e.g., less sensitive) during first-tier sensing/analysis, and may be lower (e.g., more sensitive) during second-tier sensing for those sensors/analyzers that did not detect a triggering event as first-tier sensors/analyzers. For example, when a first-tier ECG sensor/analyzer produces a trigger signal (e.g., signal 532, FIG. 5), but a heart sound sensor/analyzer does not produce a trigger signal, a lower threshold value may be set or selected for the heart sound sensor/analyzer for its analysis performed as a second-tier sensor/analyzer. Such a system may have a relatively high sensitivity, meaning that the system may be adapted to produce an alarm, external system notification, and/or cardiac stimulus at relatively lower second-tier thresholds than other embodiments. Method embodiments for such systems are discussed below, in conjunction with FIG. 7.

Figure 7:
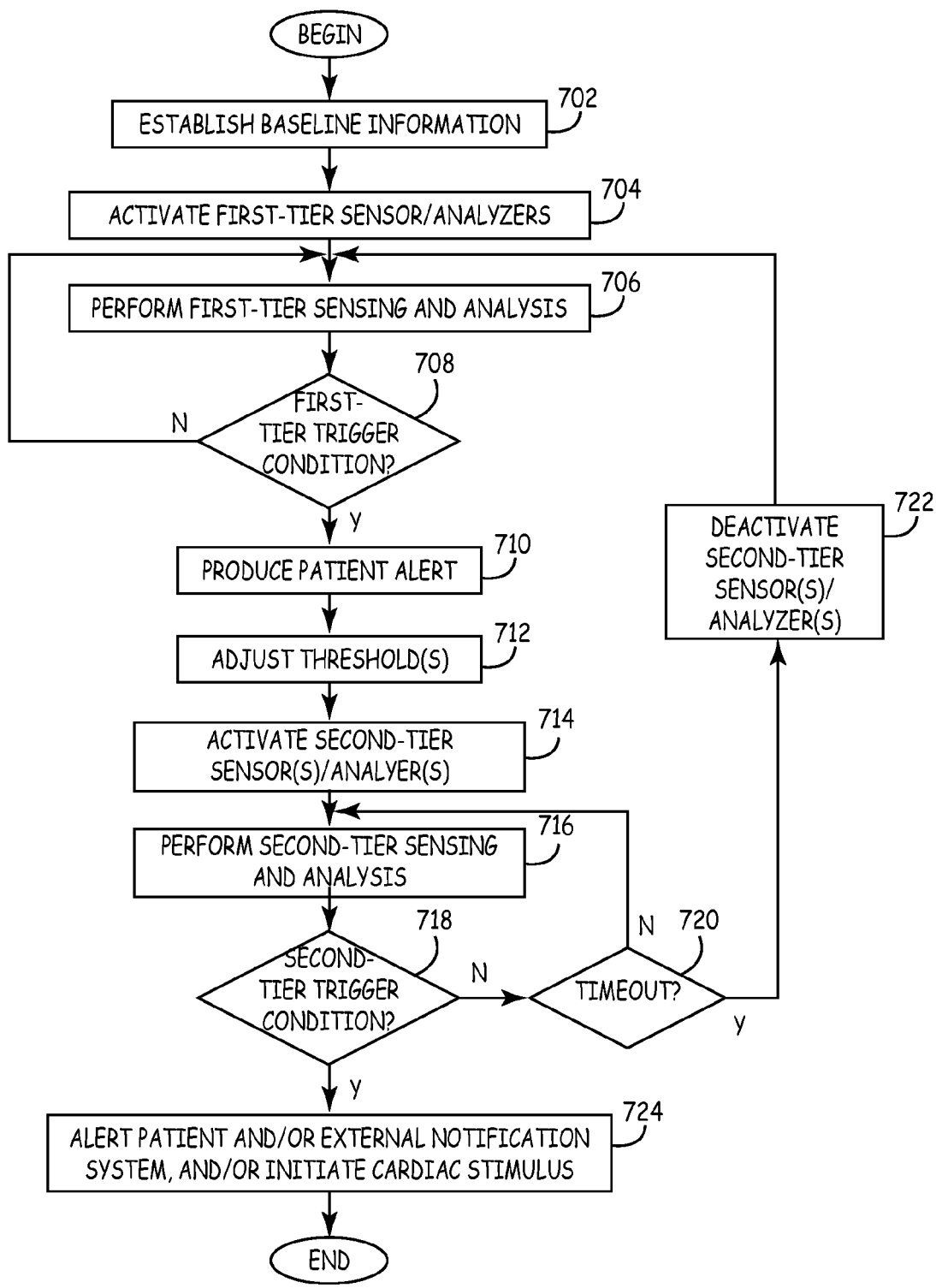
FIG. 7 illustrates a flowchart of a method for detecting myocardial ischemia, in accordance with another example embodiment.

FIG. 7 illustrates a flowchart of a method for detecting myocardial ischemia, in accordance with another example embodiment. The method begins, in an embodiment, by establishing baseline information for the patient, in block 702. Establishing baseline information may be performed in ways that are substantially similar to ways discussed in conjunction with block 602 (FIG. 6). For purposes of brevity, that discussion is not repeated here.

Unless already activated, a plurality of first-tier sensors/analyzers (e.g., first-tier sensors 502-504 and analyzers 506-508, FIG. 5) may be activated, in block 704. In an embodiment, the first-tier sensors/analyzers include an ECG sensor/analyzer, a heart sound sensor/analyzer, and possibly one or more other types of sensors/analyzers (e.g., vibration sensor/analyzer, pressure sensor/analyzer, change in pressure with time (dp/dt) sensor/analyzer, magnetic sensor/analyzer, hall sensor/analyzer, biomarker level sensor/analyzer, oxygen level sensor/analyzer, carbon dioxide level sensor/analyzer, glucose sensor/analyzer, pH sensor/analyzer, body temperature sensor/analyzer, heart rate sensor/analyzer, heart rate variability sensor/analyzer, heart wall motion sensor/analyzer, impedance sensor/analyzer, optical sensor/analyzer, respiration sensor/analyzer, and/or a patient activator).

In block 706, first-tier sensing and analysis is performed, as was discussed previously in conjunction with elements 502-504 and 506-508 of FIG. 5. For example, in an embodiment, first-tier sensing and analysis may include taking ECG readings, producing a current ECG waveform, comparing the current ECG waveform to baseline ECG information, and determining whether the difference between the current ECG waveform and the baseline ECG information meets or exceeds a threshold. In another embodiment, first-tier sensing and analysis may include taking ECG readings, producing a current ECG waveform, and determining whether one or more portions of the ECG waveform (e.g., an ST segment 210 or 310, FIG. 2 or 3) meet or exceed a threshold. When the difference between the current ECG waveform and the baseline ECG information meets or exceeds a threshold, or when one or more portions of the ECG waveform meet or exceed a threshold, a positive trigger signal (e.g., trigger signal 532, FIG. 5) may be produced.

First-tier sensing and analysis may also include taking heart sound readings, producing a current heart sound waveform, comparing the current heart sound waveform to baseline heart sound information, and determining whether the difference between the current heart sound waveform and the baseline heart sound information meets or exceeds a threshold. In another embodiment, first-tier sensing and analysis may include taking heart sound readings, producing a current heart sound waveform, and determining whether a third heart sound (e.g., heart sound 324, FIG. 3) and/or a fourth heart sound (e.g., heart sound 326, FIG. 3) are present to an extent that they meet or exceed a threshold. When a third heart sound and/or a fourth heart sound are present to an extent that they meet or exceed a threshold, a positive trigger signal (e.g., trigger signal 533, FIG. 5) may be produced. In other embodiments, where different types of sensors/analyzers are used as the first-tier sensors/analyzers, different types of sensing and analysis would be performed.

In block 708, a determination is made whether a first-tier trigger condition has occurred. In an embodiment, a first-tier trigger condition has occurred when a positive trigger signal is produced by a first-tier sensor/analyzer (e.g., an ECG sensor/analyzer, heart sound sensor/analyzer, or other type of sensor/analyzer), as discussed above. When a first-tier trigger condition has not occurred, the method iterates as shown. When a first-tier trigger condition has occurred, then a patient alert may be produced, in block 710. As discussed previously in conjunction with block 526 (FIG. 5), a patient alert may include an audible or vibratory alert, and/or an audible or displayed message. In an alternate embodiment, a patient alert may not be produced at this point.

In block 712, the thresholds for those sensors/analyzers that did not produce a trigger signal may be adjusted to values that increase their sensitivity (e.g., to lower values). In addition or alternatively, in block 714, one or more additional second-tier sensors/analyzers may be activated.

In block 716, second-tier sensing and analysis is performed, as was discussed previously in conjunction with elements 516-518 and 520-522 of FIG. 5. For example, in an embodiment, second-tier sensing and analysis may include additional ECG sensing/analysis, heart sound sensing/analysis, vibration sensing/analysis, magnetic sensing/analysis, biomarker level sensing/analysis, oxygen level sensing/analysis, body temperature sensing/analysis, pressure sensing/analysis, and/or patient activator input sensing/analysis. In other embodiments, where one or more different types of sensor/analyzers are used as the second-tier sensors/analyzers, different types of sensing and analysis would be performed. The second-tier sensing and analysis may result in one or more positive trigger signals (e.g., trigger signals 540-542, FIG. 5).

In block 718, a determination is made whether a second-tier trigger condition has occurred. In an embodiment, a second-tier trigger condition has occurred when a positive trigger signal is produced by a second-tier sensor/analyzer (e.g., an ECG sensor/analyzer, a heart sound sensor/analyzer, or another type of sensor/analyzer), as discussed above. When a second-tier trigger condition has not occurred, a determination is made whether a second-tier sensing timeout has occurred, in block 720. A second-tier sensing timeout may be on the order of minutes to hours, in an embodiment. When a second-tier sensing timeout has not occurred, the method continues to perform second-tier sensing/analysis, as shown. When a second-tier sensing timeout has occurred, the second-tier sensors/analyzers may be deactivated, in block 722, and the method returns to performing first-tier sensing/analysis, as shown.

Referring again to block 718, when a second-tier trigger condition has occurred, then a patient alert may be produced, an external notification system may be contacted, and/or a cardiac stimulus may be initiated, in block 724. As discussed previously in conjunction with blocks 526, 528, and 529 (FIG. 5), a patient alert may include an audible or vibratory alert, and/or an audible or displayed message. Contacting an external notification system may include sending a message to a patient communication device (e.g., device 408, FIG. 4) or a computing device (e.g., device 410, FIG. 4) indicating that myocardial ischemia may be occurring. Initiating a cardiac stimulus may include producing a stimulus to the heart tissue (e.g., defibrillation stimulus, pacing stimulus, pacing rate adjustment, pacing characteristic adjustment, and/or pulse adjustment stimulus). The method may then end.

Embodiments of the inventive subject matter may provide one or more technical, economic or other advantages over traditional systems. For example, embodiments of the inventive subject matter may provide rapid detection and patient alert at the onset of myocardial ischemia. In some cases, the rapid detection and alert may result in a shorter period of delay between the onset of myocardial ischemia and the application of proper medical therapies. Accordingly, reduced cell necrosis and mortality rates may be achieved. In an embodiment, all or portions of the system or apparatus may be cycled on or off to conserve battery power. For example, all or portions of the system or apparatus may be cycled on when a patient is most likely to be susceptible to myocardial ischemia (e.g., during early morning hours and/or during heavy exertion).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the inventive subject matter. Rather, the foregoing detailed description will provide those skilled in the art with a convenient road map for implementing an embodiment of the inventive subject matter, it being understood that various changes may be made in the function and arrangement of elements described without departing from the scope of the inventive subject matter as set forth in the appended claims and their legal equivalents.

The invention claimed is:

1. A heart monitoring apparatus adapted to detect myocardial ischemia, the apparatus comprising:
   at least one first-tier sensor/analyzer adapted to sense a first input related to cardiac function, and to produce a first-tier trigger signal when the first input indicates myocardial ischemia; and
   at least one second-tier sensor/analyzer adapted to sense a second input related to cardiac function, and to produce a second-tier trigger signal when the second input indicates myocardial ischemia;
   a control element adapted to adjust at least one threshold for at least one second-tier sensor/analyzer when the first-tier trigger signal is produced; and
   a triggering element adapted to produce a response-invoking signal in response to the first-tier trigger signal and the second-tier trigger signal.

2. The heart monitoring apparatus of claim 1, further comprising:
   a patient alert element adapted to produce an alert in response to the response-invoking signal.

3. The heart monitoring apparatus of claim 1, further comprising:
   an external system notification element adapted to send a message to an external system in response to the response-invoking signal.

4. The heart monitoring apparatus of claim 1, further comprising:
   a cardiac stimulus element adapted to produce a stimulus to heart tissue in response to the response-invoking signal.

5. The heart monitoring apparatus of claim 1, wherein the at least one first-tier sensor/analyzer includes an electrocardiogram (ECG) sensor/analyzer.

6. The heart monitoring apparatus of claim 1, wherein the at least one first-tier sensor/analyzer includes at least one patient activator with which a patient may indicate a presence of a symptom.

7. The heart monitoring apparatus of claim 1, wherein the at least one first-tier sensor/analyzer includes a heart sound sensor/analyzer.

8. The heart monitoring apparatus of claim 1, wherein the at least one second-tier sensor/analyzer includes one or more inactivated second-tier sensors/analyzers, the apparatus further comprising:
a second-tier initiation control element adapted to activate at least one of the inactivated second-tier sensors/analyzers when the first-tier trigger signal is produced.

9. The heart monitoring apparatus of claim 1, wherein the control element is adapted to adjust at least one threshold for the at least one first-tier sensor/analyzer.

10. The heart monitoring apparatus of claim 1, wherein the at least one first-tier sensor/analyzer includes a plurality of sensors/analyzers selected from a group of sensors/analyzers that includes an ECG sensor/analyzer, a heart sound sensor/analyzer, a vibration sensor/analyzer, a pressure sensor/analyzer, a change in pressure with time (dp/dt) sensor/analyzer, a magnetic sensor/analyzer, a hall sensor/analyzer, a biomarker level sensor/analyzer, an oxygen level sensor/analyzer, a carbon dioxide level sensor/analyzer, a glucose sensor/analyzer, a pH sensor/analyzer, a temperature sensor/analyzer, a heart rate sensor/analyzer, a heart rate variability sensor/analyzer, a heart wall motion sensor/analyzer, an impedance sensor/analyzer, an optical sensor/analyzer, a respiration sensor/analyzer, and a patient activator.

11. The heart monitoring apparatus of claim 1, wherein the at least one second-tier sensor/analyzer includes a heart sound sensor/analyzer.

12. The heart monitoring apparatus of claim 1, wherein the at least one second-tier sensor/analyzer includes a plurality of sensors/analyzers selected from a group of sensors/analyzers that includes an ECG sensor/analyzer, a heart sound sensor/analyzer, a vibration sensor/analyzer, a pressure sensor/analyzer, a change in pressure with time (dp/dt) sensor/analyzer, a magnetic sensor/analyzer, a hall sensor/analyzer, a biomarker level sensor/analyzer, an oxygen level sensor/analyzer, a carbon dioxide level sensor/analyzer, a glucose sensor/analyzer, a pH sensor/analyzer, a temperature sensor/analyzer, a heart rate sensor/analyzer, a heart rate variability sensor/analyzer, a heart wall motion sensor/analyzer, an impedance sensor/analyzer, an optical sensor/analyzer, a respiration sensor/analyzer, and a patient activator.

13. A heart monitoring apparatus adapted to detect myocardial ischemia, the apparatus comprising:
an electrocardiogram (ECG) sensor/analyzer adapted to sense bioelectrical activity, to produce a current ECG waveform, and to produce an ECG trigger signal when at least a portion of the current ECG waveform indicates myocardial ischemia;
a heart sound sensor/analyzer adapted to sense heart sounds, to produce a current heart sound waveform, and to produce a heart sound trigger signal when at least a portion of the current heart sound waveform indicates myocardial ischemia;
an initiation control element adapted to activate the heart sound sensor/analyzer in response to the ECG trigger signal; and
a triggering element adapted to produce a response-invoking signal in response to the ECG trigger signal and the heart sound trigger signal.

14. The heart monitoring apparatus of claim 13, wherein the ECG sensor/analyzer is adapted to produce the ECG trigger signal when a difference between an ST segment of the current ECG waveform and an ST segment of a baseline ECG waveform meets or exceeds a threshold value.

15. The heart monitoring apparatus of claim 13, wherein the ECG sensor/analyzer is adapted to produce the ECG trigger signal when an ST segment of the current ECG waveform exceeds a threshold value.

16. The heart monitoring apparatus of claim 13, wherein the heart sound sensor/analyzer is adapted to produce the heart sound trigger signal when a difference between a portion of the current heart sound waveform corresponding to a fourth heart sound and a portion of a baseline heart sound waveform corresponding to the fourth heart sound meets or exceeds a threshold value.

17. The heart monitoring apparatus of claim 13, wherein the heart sound sensor/analyzer is adapted to produce the heart sound trigger signal when a difference between a portion of the current heart sound waveform corresponding to a third heart sound and a portion of a baseline heart sound waveform corresponding to the third heart sound meets or exceeds a threshold value.

18. The heart monitoring apparatus of claim 13, wherein the heart sound sensor/analyzer is adapted to produce the heart sound trigger signal when a portion of the heart sound waveform that corresponds to a fourth heart sound exceeds a threshold value.

19. The heart monitoring apparatus of claim 13, wherein the heart sound sensor/analyzer is adapted to produce the heart sound trigger signal when a portion of the heart sound waveform that corresponds to a third heart sound exceeds a threshold value.

20. The heart monitoring apparatus of claim 13, further comprising:
a patient alert element adapted to produce an alert in response to the response-invoking signal.

21. The heart monitoring apparatus of claim 13, further comprising:
an external system notification element adapted to send a message to an external system in response to the response-invoking signal.

22. The heart monitoring apparatus of claim 13, further comprising:
a cardiac stimulus element adapted to produce a stimulus to heart tissue in response to the response-invoking signal.

23. The heart monitoring apparatus of claim 13, further comprising at least one additional sensor/analyzer selected from a group of sensors/analyzers that includes an ECG sensor/analyzer, a heart sound sensor/analyzer, a vibration sensor/analyzer, a pressure sensor/analyzer, a change in pressure with time (dp/dt) sensor/analyzer, a magnetic sensor/analyzer, a hall sensor/analyzer, a biomarker level sensor/analyzer, an oxygen level sensor/analyzer, a carbon dioxide level sensor/analyzer, a glucose sensor/analyzer, a pH sensor/analyzer, a temperature sensor/analyzer, a heart rate sensor/analyzer, a heart rate variability sensor/analyzer, a heart wall motion sensor/analyzer, an impedance sensor/analyzer, an optical sensor/analyzer, a respiration sensor/analyzer, and a patient activator.

* * * * *